United States Patent [19]

Gustafson et al.

[11] Patent Number: 4,837,368

[45] Date of Patent: Jun. 6, 1989

[54] LOW PRESSURE CATALYTIC HYDROGENATION OF CARBONYL-CONTAINING COMPOUNDS AND SUPPORTED CATALYSTS THEREFOR

[75] Inventors: Bruce L. Gustafson; Paul S. Wehner, both of Kingsport, Tenn.

[73] Assignee: Eastman Kodak Company, Rochester, N.Y.

[21] Appl. No.: 150,791

[22] Filed: Feb. 1, 1988

[51] Int. Cl.$^4$ .................................. C07C 29/14
[52] U.S. Cl. ................................ 568/881; 568/880
[58] Field of Search ............... 568/814, 876, 880, 881, 568/861, 862, 885, 846

[56] References Cited

U.S. PATENT DOCUMENTS

| | | | |
|---|---|---|---|
| 2,351,302 | 6/1944 | Staudinger et al. | 568/863 |
| 2,867,663 | 1/1959 | Lacey | 568/881 |
| 3,334,149 | 8/1967 | Akin et al. | 260/617 |
| 3,715,404 | 2/1973 | Lindlar et al. | 568/814 |
| 4,100,180 | 7/1978 | Ichikawa et al. | 568/881 |
| 4,105,674 | 8/1978 | De Thomas et al. | 260/343.6 |
| 4,149,021 | 4/1979 | Wall | 568/864 |
| 4,283,581 | 8/1981 | Wilkes | 568/864 |
| 4,346,240 | 8/1982 | Grey et al. | 568/885 |
| 4,398,039 | 8/1983 | Pesa et al. | 560/265 |
| 4,409,395 | 10/1983 | Miyazaki | 560/179 |
| 4,518,714 | 5/1985 | Gustafson | 518/721 |

FOREIGN PATENT DOCUMENTS

| | | | |
|---|---|---|---|
| 744410 | 7/1970 | Belgium | 568/874 |
| 0008767 | 3/1980 | European Pat. Off. | 568/881 |
| 74193 | 3/1983 | European Pat. Off. | 568/884 |
| 0074193 | 3/1983 | European Pat. Off. | 568/881 |
| 143634 | 5/1985 | European Pat. Off. | 568/884 |
| 175558 | 3/1986 | European Pat. Off. | 568/884 |
| 210795 | 2/1987 | European Pat. Off. | . |
| 2206805 | 8/1973 | Fed. Rep. of Germany | 568/814 |
| WO82/03854 | 6/1982 | PCT Int'l Appl. | . |
| 1534232 | 11/1978 | United Kingdom | 568/884 |

OTHER PUBLICATIONS

Wehner, et al., "XPS Study of the Reduction in Reoxidation of ZnO-Supported Palladium", Journal of Catalysis, vol. 88, pp. 246-248, 1984.

Sokolskii, et al., "Catalytic Properties of Palladium Oxide Systems in the Hydrogenation of Crotonaldehyde", React. Kinet. Catal. Lett., vol. 30, pp. 101-104 (1986).

*Primary Examiner*—Werren B. Lone
*Attorney, Agent, or Firm*—S. E. Reiter; William P. Heath, Jr.

[57] ABSTRACT

Process for the hydrogenation of carbonyl-containing compounds at mild conditions of temperature and pressure to produce alcohols or amines is disclosed, employing catalysts comprising palladium and zinc on an inorganic support. A method for the preparation of these supported catalysts which are useful for the desired reductive conversion is also disclosed.

33 Claims, No Drawings

LOW PRESSURE CATALYTIC HYDROGENATION OF CARBONYL-CONTAINING COMPOUNDS AND SUPPORTED CATALYSTS THEREFOR

DESCRIPTION

This invention relates to catalytic hydrogenation. In one aspect, the present invention relates to a process for the selective reduction of carbonyl-containing compounds to alcohols. In another aspect, the present invention relates to supported catalysts useful for the selective reduction of carbonyl-containing compounds to alcohols, and methods for preparing such catalysts.

BACKGROUND OF THE INVENTION

The catalytic hydrogenation of carbonyl-containing compounds, e.g., esters, to produce their corresponding alcohols, is potentially of great commercial value. Catalysts traditionally employed for such conversions include copper chromite based materials, frequently containing a promoter such as barium. Unfortunately, these catalysts typically require high pressure to achieve commercially attractive reaction rates for the hydrogenation of esters, i.e., pressures in excess of 3000 psig. In addition, chromium and barium present toxicity and environmental concerns which must be dealt with if one is to economically and safely use these materials on a commercial scale.

More recently, substantial amounts of research have been carried out in efforts to develop hydrogenation catalysts capable of reducing carbonyl-containing compounds, e.g., organic acids and esters, to alcohols at reduced pressures. While such catalysts are capable of promoting the hydrogenation of carbonyl-containing compounds to produce alcohols, one problem with such materials is the need to run at very low liquid hourly space velocities in order to achieve suitably high conversion levels.

Another problem frequently encountered with such prior art low pressure catalyst systems when employed for the reduction of carbonyl-containing compounds such as aldehydes and ketones, is their lack of selectivity to the desired alcohol product, such catalysts frequently being too active and thus producing product which results from reaction of substrate with additional hydrogen.

Yet another problem encountered with such prior art low pressure catalyst systems, such as Raney nickel, is the ease of handling of such catalysts, which are frequently pyrophoric, and thus require special handling to avoid fire hazard.

OBJECTS OF THE INVENTION

An object of the present invention, therefore, is a process for the low pressure, high selectivity, high activity hydrogenation of carbonyl-containing compounds to produce alcohols.

Another object of the present invention is a catalyst system which is capable of promoting the hydrogenation of carbonyl-containing compounds at low reaction pressures.

Still another object of the present invention is a catalyst system which is capable of promoting the hydrogenation of carbonyl-containing compounds at low reaction pressure, is readily prepared and requires no special handling precautions.

These and other objects of the present invention will become apparent from inspection of the detailed description and the appended claims which follow.

STATEMENT OF THE INVENTION

In accordance with the present invention, we have discovered that palladium and zinc supported on a carrier is an effective catalyst for the low pressure hydrogenation of carbonyl-containing compounds to selectively produce alcohols in high yield. The invention process employs readily prepared, easily handled catalysts and enables a commercially important reaction, i.e., the conversion of carbonyl-containing compounds to alcohols, to be carried out at low reaction pressures, thereby reducing the cost of equipment required for the desired hydrogenation reaction and reducing the safety risks involved in such conversions.

DETAILED DESCRIPTION OF THE INVENTION

In accordance with the present invention there is provided a method for preparing high activity, low pressure hydrogenation catalysts comprising palladium and zinc on a support, which method comprises:
(a) contacting said support with at least one of zinc or a reducible compound thereof and palladium or a reducible compound thereof;
(b) optionally calcining the resulting palladium and/or zinc treated support in the presence of an oxygen-containing gas at a temperature in the range of 200° up to 400° C. for a time sufficient to activate said palladium and/or said zinc component;
(c) where palladium is employed in step (a), optionally contacting said palladium-treated support with a reducing atmosphere under conditions sufficient to cause reduction of at least a portion of the palladium to less than the +2 oxidation state;
(d) optionally contacting said support again with at least one member selected from the group consisting of palladium or a reducible compound thereof and zinc or a reducible compound thereof; with the proviso that said support is ultimately contacted with both palladium and zinc;
(e) optionally calcining the resulting palladium and zinc treated support in the presence of an oxygen-containing gas at a temperature in the range of 200° up to 400° C. for a time sufficient to activate said palladium and said zinc component; and thereafter
(f) contacting the zinc and palladium-treated support with a reducing atmosphere under conditions sufficient to cause reduction of at least a portion of the palladium to less than the +2 oxidation state.

As suggested by the above-described method for catalyst preparation, support can be contacted simultaneously with appropriate palladium and/or zinc components; or support can be contacted with one component followed by a subsequent contacting with the other component; or support can be treated via multiple contacting (with optional calcination/reduction treatments between contacting) with one or both of the palladium and zinc catalyst components.

In accordance with another embodiment of the present invention, there is provided a process for the low pressure hydrogenation of carbonyl-containing compounds of specified structure to produce the corresponding alcohols, which process comprises contacting the carbonyl-containing compounds with a catalyst comprising palladium and zinc on a support, wherein the quantity of palladium employed falls within the range of 0.01 up to 20 weight percent, calculated as the metal and based on the total weight of palladium, zinc and support; and wherein the atomic ratio of Pd to Zn falls within the range of about 0.01 up to 10; preferably in the range of about 0.2 up to 5.0; wherein said contacting is carried out in the presence of hydrogen under hydrogenation conditions.

Catalysts employed in the practice of the present invention comprise palladium and zinc on a carrier or support. A wide variety of techniques for contacting support with palladium and zinc are contemplated for use in the practice of the present invention. For example, palladium or a palladium precursor can be applied directly to support employing such techniques as incipient wetness, wet impregnation, ion exchange, metal atom evaporation, precipitation; then zinc or a zinc precursor can be similarly applied to support; or support can be contacted with both zinc and palladium at the same time; or appropriate precursors of palladium and zinc can be coprecipitated in the presence of support, and then calcined and/or reduced to convert the palladium and zinc to an active form.

A wide range of zinc compounds are suitable sources of zinc for use in the practice of the present invention, e.g., zinc nitrate, zinc halides, zinc acetate, zinc carbonate, zinc oxide and the like.

Suitable sources of palladium are any compounds which are reducable when subjected to reducing conditions. Since many palladium compounds are convertible to the oxide form upon calcination under the above-described conditions, and the oxides of palladium are readily reduced, many palladium compounds are useful for catalyst preparation. Exemplary palladium compounds include the palladium halides, palladium acetate, palladium nitrate, palladium ammine complexes, organometallic complexes of palladium, and the like.

The surface area of the catalyst supports employed in the practice of the present invention can vary widely. Preferably, support materials having surface areas of at least about 1 m$^2$/g will be employed. Of course, those of skill in the art also recognize that higher surface area materials will generally produce higher activity catalysts than lower surface area catalysts having comparable composition.

A wide range of inorganic materials can be employed as support for the invention Pd/Zn catalysts. Exemplary materials are relatively non-acidic in that they do not promote significant levels of such undesired side reaction as transesterification, alcohol dehydration, ester hydrolysis, and the like. Such materials include silica (SiO$_2$), titania (TiO$_2$), carbon (C), rare earth oxides (e.g., La$_2$O$_3$, CeO$_2$), and the like, as well as mixtures of any two or more thereof.

When the palladium and/or zinc components of the invention catalyst are provided as precursor moieties, it is preferred to subject the Pd/Zn-treated support to a calcination treatment at temperatures in the range of about 200° up to 400° C. Such temperature is maintained for a time sufficient to activate the zinc and the palladium components used to form the catalyst. Times in the range of about 2 up to 8 hours or longer are generally effective for this purpose.

Finally, the Pd/Zn-treated support is subjected to a reducing atmosphere under conditions sufficient to cause reduction of at least a portion of the palladium to less than the +2 oxidation state.

The term "carbonyl-containing compounds" as employed in this specification is intended to include compounds of the structure.

wherein R is a C$_1$–C$_{20}$ alkyl or substituted alkyl radical (including cycloalkyl radicals); or
a C$_2$–C$_{20}$ alkenyl (including cycloalkenyl) or alkynyl (including cycloalkynyl) radical or substituted derivative thereof;
wherein said substituted groups include ethers, amines, additional carbonyl groups, aryl groups, hydroxyl groups and alkoxy groups; and
Z=H,
R', wherein R' is selected from R, C$_6$–C$_{20}$ aryl or substituted aryl and is selected independently of R,
OR', wherein R' is as defined above,
X, wherein X is any one of the halogens,
NR''$_2$, wherein each R'' is independently selected from H or R';
with the proviso that R and Z can be joined as part of a polymethylene or hydrocarbyl or heteroatom-substituted polymethylene radical, poly-carbonyl analogs of such carbonyl-containing compounds; and
mixtures of any two or more thereof.

Preferred carbonyl-containing compounds are compounds selected from the group consisting of:

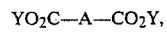 (a)

wherein A is an alkylene moiety, an alkenylene moiety, or an alkynylene moiety having 1 up to 20 carbon atoms, or substituted derivative thereof, or a cycloalkyl or cycloalkenyl moiety having 4–12 carbon atoms or substituted derivative thereof; and wherein each Y is independently a C$_1$ up to C$_{12}$ alkyl, alkenyl or alkynyl radical or substituted derivative thereof;

 (b)

wherein B is an alkyl, cycloalkyl, alkenyl, cycloalkenyl, alkynyl or cycloalkynyl radical, or substituted derivative thereof, having 1 up to 20 carbon atoms; and
wherein Y is defined as above:

 (c)

wherein Q is an alkyl, cycloalkyl, alkenyl, cycloalkenyl, alkynyl or cycloalkynyl radical having 1 up to 20 carbon atoms or substituted derivatives thereof; and
mixtures of any two or more thereof.

Exemplary carbonyl-containing compounds which satisfy the above formulae include alkyl oleates, dialkyl adipates, propionaldehyde, dialkyl, cyclohexane dicarboxylates, alkyl acrylates, alkyl propionates, alkyl isobutyrates, alkyl normal butyrates, alkyl acetates, nonanal, dialkyl butane dicarboxylates, alkyl methacrylates, alkyl crotonates, alkyl sorbates, alkyl cinnamates, maleic anhydride, alkyl fumarates, dialkyl succinates, succinic anhydride, alkyl glutarates, dialkyl malonates, dialkyl octanedioates, dialkyl decanedioates, dialkyl dodecanedioates, alkyl laurates, alkyl myristates, alkyl palmitates, alkyl stearates, alkyl linoleates, alkyl linolenates, alkyl isovalerates, alkyl normal valerates, alkyl caproates, alkyl caprylates, alkyl 2-ethylhexanoates, dialkyl cyclohexanedioates, γ-butyrolactone, alkyl phenylacetates, alkyl cyclohexane carboxylates, alkyl pyruvates, alkyl gylcolates, alkyl oxalates, alkyl formates, alkyl lactates, alkyl citrates, glyceride esters, and the like.

Typical alkyl groups employed have from 1 up to 20 carbon atoms, with alkyl groups having 1 up to 6 carbon atoms being preferred.

The hydrogenation process of the present invention involves contacting at least one of the above-described carbonyl-containing compounds with at least one of the above-described supported palladium/zinc catalysts in the presence of hydrogen under hydrogenation conditions. Hydrogenation conditions typically employed in the practice of the present invention are set forth below.

The process of the present invention can be operated in a variety of configurations. Depending on the substrate to be hydrogenated, the preferred method of opeation is frequently in a fixed bed flow reaction system. If the vapor pressure of the substrate to be hydrogenated is sufficiently high at reaction temperature, the desired method of operation may be vapor phase, i.e., all reactants and products exist in the gaseous phase. For other substrates, the desired method of operation may be a trickle bed configuration. Regardless of the method of operation, the desired time of contact between the reactants and catalyst components can be varied as desired to achieve the desired level of reaction.

In typical fixed bed operation, pressures in the range of 100–10,000 psig will be employed. Preferably, the pressure will be in the range of 100–3500 psig. Similarly, temperatures in the range of 25°–400° C. can be used, with a more preferred range of 100°–350° C. While the feed rate of the substrate will be varied to control the level of conversion, normal liquid hourly space velocities (LHSV) will be in the range of about 0.01–100 $h^{-1}$, with a preferred range of 0.1–20 $h^{-1}$. The molar ratio of hydrogen to substrate will typically be in the range of 1:1 to 1000:1 with a preferred range of 2:1 to 100:1.

Alternatively the invention may be conducted in a slurry phase reactor. In slurry phase operation, the ratio of carbonyl-containing compound to catalyst employed can vary widely, with ratios as low as 1:1 or lower being operable, but not economically attractive; and ratios as high as 10,000:1 and higher also being operable, but generally providing relatively low conversions unless very long contact times are employed. Preferred carbonyl-containing compound:catalyst ratios fall within the range of about 1:1 up to 1,000:1, with ratios in the range of about 2:1 up to 100:1 being most preferred because good levels of conversion of the carbonyl-containing compounds are obtained without requiring excessive amounts of catalyst, or extremely long contact times.

While the invention hydrogenation process can be carried out in the absence of solvent, it is presently preferred to perform the process in the presence of a suitable solvent. Suitable solvents are compounds which are fluid and in which the carbonyl-containing starting material is soluble at reaction temperature, and which are non-reactive under hydrogenation conditions. Preferred solvents are those which are fluid and in which the carbonyl-containing starting material is soluble at room temperature. Exemplary solvents include aromatic solvents such as toluene; alcohols such as methanol; ethers such as diphenyl ether and tetrahydrofuran; and the like.

When employed, the volume/volume ratio of solvent to substrate can vary widely, typically falling in the range of about 5:95 to 95:5.

In a preferred embodiment of the present invention, hydrogenation of carbonyl-containing compounds is carried out with small amounts of water (i.e., 0.01 up to about 2 wt. % water based on the total weight of reactants and solvent) present in the reaction mixture. It has been found that selectivity to hydrogenation (as opposed to transesterification between reactant and product) products is greatly improved by the presence of such small quantities of water in the reaction mixture.

Following hydrogenation, the desired product can be recovered and purified using conventional techniques well known to those of skill in the art. For example, catalyst can be removed from the reaction mixture by filtration, decantation and the like. By-products and unreacted starting material as well as solvent, if employed, can be separated from the product by distillation, recrystallization, solvent/solvent extraction, and the like.

The invention will now be described in greater detail by reference to the following non-limiting examples.

EXAMPLE 1

Catalyst Preparation

A sample of 1 wt % Pd on Davison Grade 59 $SiO_2$ was prepared by dissolving 0.48 grams (g) of $Pd(NO_3)_2$ in 29.4 mL of water and adding the resulting solution to about 20 g of the solid $SiO_2$ support material. The resulting solid sample was dried in air at 90° C. for 30 minutes and then further calcined in air at 350° C. for 12 hours. The resulting $Pd/SiO_2$ catalyst was split into separate fractions for zinc addition. Zinc was added by dissolving the appropriate amount of zinc nitrate in a small amount of water and adding this solution to the $Pd/SiO_2$ sample. The resulting solid was dried at 90° C. in air and then calcined at 200° C. for several hours prior to evaluation for hydrogenation of carbonyl-containing compounds.

EXAMPLE 2

Methyl Acetate Hydrogenation

Catalysts prepared as described in Example 1 were employed for the vapor phase hydrogenation of methyl acetate.

Catalytic evaluations were conducted in a vapor phase micro-reactor system using 1–2 cc of powdered catalyst. Methyl acetate feed was pumped into a heated chamber which was purged with the hydrogen feed gas. Typical GHSV were in the range of 30,000 $h^{-1}$, with $H_2$/ester ratios in the range of 3.6 up to 4.5 being typical. Product analysis of exit stream from the reactor was accomplished by gas chromatography. Results obtained at 300° C., 750 psig, at conversions of <20% are presented in Table 1.

TABLE 1

Methyl Acetate Hydrogenation

| Catalyst | Rate (μmole/g-cat sec) | | | |
|---|---|---|---|---|
| | MeOH | EtOH | EtOAc | Total* |
| Pd/SiO$_2$ | 1.21 | 0.016 | 0.073 | 0.089 |
| Pd—Zn/SiO$_2$ (1:1)** | 2.74 | 0.024 | 0.85 | 0.87 |
| Pd—Zn/SiO$_2$ (1:2)** | 6.48 | 0.12 | 2.25 | 2.37 |
| Pd—Zn/SiO$_2$ (1:5)** | 3.09 | 0.00 | 0.84 | 0.84 |
| Pd—Zn/SiO$_2$ (1:10)** | 2.31 | 0.012 | 0.68 | 0.69 |
| Zn/SiO$_2$ | 0.00 | 0.00 | 0.00 | 0.00 |

MeOH = Methanol, EtOH = Ethanol, EtOAc = Ethyl Acetate
*Total = Rate EtOH + Rate EtOAc
**The numbers in parenthesis indicate the atomic ratio of Pd:Zn.

The results set forth in Table 1 demonstrate that supporting palladium and zinc on silica results in catalysts with performance superior to the corresponding supported monometallic samples.

EXAMPLE 3

Hydrogenation of Methyl Acetate

A series of catalysts similar to those described above were prepared except that the Pd was added using an ion exchange technique and the Pd loading level was 2.8 wt %. The catalysts were prepared by treating the SiO$_2$ sample with NH$_4$OH and Pd(NH$_3$)$_4$Cl$_2$ (pH=11.0) for 80 minutes, filtering the solid material from solution, rinsing with water, and drying at 120° C. for 24 hours. Addition of zinc was accomplished according to Example 1. The resulting samples were calcined for about 3 hours at about 200° C. prior to evaluation for catalytic activity. Results from this catalytic evaluation using the conditions employed in Example 2 are presented in Table 2.

TABLE 2

Methyl Acetate Hydrogenation

| Catalyst | Rate (μmole/g-cat sec) | | | |
|---|---|---|---|---|
| | MeOH | EtOH | EtOAc | Total* |
| Pd—Zn (1:0) | 3.17 | 0.02 | 0.86 | 0.89 |
| Pd—Zn (1:1) | 5.70 | 3.65 | 1.35 | 5.00 |
| Pd—Zn (1:2) | 8.72 | 3.73 | 3.05 | 6.78 |
| Pd—Zn (1:5) | 4.60 | 0.41 | 2.18 | 2.59 |
| Pd—Zn (0:1) | 0.00 | 0.00 | 0.00 | 0.00 |

MeOH = Methanol, EtOH = Ethanol, EtOAc = Ethyl Acetate
*Total = Rate EtOH + Rate EtOAc The results set forth in Table 2 indicate that catalysts prepared by ion exchange of the palladium component exhibit activity for the low pressure hydrogenation of carbonyl compounds. In addition, it is evident that catalyst performance is dependent on the Pd-Zn ratio. At lower Pd-Zn ratios, selectivity to the alcohol is enhanced, but the overall rate of hydrogenation is lower than observed at higher Pd-Zn ratios. Thus, the Pd-Zn ratio can be used to adjust the rate of hydrogenation.

EXAMPLE 4

A series of catalysts were prepared using the procedure described in Example 3 except that the palladium loading level was varied from 1–15 wt % and the Pd-Zn atomic ratio was held constant at 1:2. These catalysts were evaluated as set forth in Example 2. For comparison, results from a 1% Pd on ZnO supported catalyst described in co-pending application Ser. No. 81,252 are shown. Data from this latter catalyst were collected under identical conditions except that the total pressure was 730 psig.

TABLE 3

Methyl Acetate Hydrogenation

| Catalyst | Rate (μmole/g-cat sec) | | | |
|---|---|---|---|---|
| | MeOH | EtOH | EtOAc | Total* |
| 1% Pd—Zn/SiO$_2$ | 4.2 | 0.8 | 1.8 | 2.6 |
| 2.8% Pd—Zn/SiO$_2$ | 8.7 | 3.7 | 3.1 | 6.8 |
| 5% Pd—Zn/SiO$_2$ | 30.4 | 6.0 | 14.5 | 20.5 |
| 1% Pd/ZnO | 7.3 | 2.0 | 3.6 | 5.6 |

MeOH = Methanol, EtOH = Ethanol, EtOAc = Ethyl Acetate
*Total = Rate EtOH + Rate EtOAc These results demonstrate that higher palladium loading levels give catalysts having dramatically higher activity for ester hydrogenation.

EXAMPLE 5

Hydrogenation of Ethyl Acetate

The catalyst prepared as described in Example 4 and containing 5 weight % Pd was used for the hydrogenation of ethyl acetate according to the procedure set forth in Example 2, except that ethyl acetate was used instead of methyl acetate.

The conversion of ethyl acetate to ethanol proceeded at a rate of about 30 μmoles/g-cat sec, thereby demonstrating that Pd-Zn/SiO$_2$ is an effective catalyst for the hydrogenation of ethyl acetate.

EXAMPLE 6

Hydrogenation of Methyl Propionate

The catalyst prepared as described in Example 4 and containing 5 weight % was used for the hydrogenation of methyl propionate to produce n-propanol, employing the procedure set forth in Example 2, except that methyl propionate was used instead of methyl acetate.

The conversion of methyl propionate to n-propanol proceeded at a rate of about 14 μmoles/g-cat sec, thereby demonstrating that Pd-Zn/SiO$_2$ catalyst is effective for the hydrogenation of methyl propionate.

EXAMPLE 7

Hydrogenation of Methyl Oleate

Fifty cc's of a 5% (Pd-Zn ratio of 1:2) on SiO$_2$ catalyst (prepared as described in Example 4) was loaded into a 1" tubular reactor. After catalyst was pre-treated at 1200 psig at 300° C. in a flowing hydrogen atmosphere for 12 hours, methyl oleate feed was pumped into the tubular reactor (maintained at 300° C.) at the rate of about 1.4 mL/minute with a hydrogen flow of about 744 standard cubic centimeters per minute.

Under the above conditions, a 9% conversion of methyl oleate was obtained with nearly quantitative selectivity to a 2:1 mixture of oleyl alcohol and stearyl alcohol.

These results demonstrate that Pd-Zn/SiO$_2$ is an effective catalyst for the selective hydrogenation of methyl oleate; with the carbon-carbon unsaturation being retained in about ⅔ of the reduced product.

EXAMPLE 8

Effect of Water Addition

Catalyst prepared as described in Example 4 and containing 5 weight % Pd was evaluated as described in Example 2, except the ester feed (methyl acetate) was supplemented with 1 weight % (based on the total weight of liquid feed) of water. The results of this experiment and a comparison in which no water was added to the feed are summarized in Table 4.

TABLE 4

Effect of Water on Methyl Acetate Hydrogenation

| Weight % Water in Feed | Rate of Formation, μmoles/g-cat sec | | | |
|---|---|---|---|---|
| | MeOH | EtOH | EtOAc | Total |
| 0.0 | 30.0 | 5.0 | 14.0 | 19.0 |
| 1.0 | 2.0 | 1.8 | 1.2 | 3.0 |

In the absence of water, transesterification product, ethyl acetate, represents more than 70% (14 out of 19 moles) of the reaction product; while in the presence of water, transesterification product represents only about 40% of the reaction product. Thus, the presence of water is seen to supress transesterification and thereby give improved selectivity to the desired direct hydrogenation product.

The examples have been provided merely to illustrate the practice of our invention and should not be read so as to limit the scope of our invention or the appended claims in any way. Reasonable variations and modifications, not departing from the essence and spirit of our invention, are contemplated to be within the scope of patent protection desired and sought.

We claim:

1. A process for the low pressure hydrogenation of carbonyl-containing compounds to produce the corresponding alcohol, wherein said carbonyl-containing compounds have the structure:

wherein R is a $C_1$-$C_{20}$ alkyl or substituted alkyl radical; or a $C_2$-$C_{20}$ alkenyl or alkynyl radical or a substituted derivative thereof;
wherein said substituted groups include ethers, amines, additional carbonyl groups, $C_6$-$C_{20}$ aryl groups, hydroxy groups and alkoxy groups; and Z is selected from the group consisting of:
H,
R', wherein R' is selected from R, $C_6$-$C_{20}$ aryl or substituted aryl, and is selected independently of R,
OR', wherein R' is as defined above,
X, wherein X is any one of the halogens, and
NR"$_2$, wherein each R" is independently selected from H or R';
with the proviso that R and Z can be joined as part of a polymethylene or hydrocarbyl- or heteroatom-substituted polymethylene radical, and
mixtures thereof;
said process comprising contacting said carbonyl-containing compounds with a catalyst comprising palladium and zinc on a support, wherein the quantity of palladium employed falls within the range of 0.01 up to 20 weight %, calculated as the metal and based on the total weight of palladium, zinc and support; and wherein the atomic ratio of Pd to Zn falls within the range of about 0.01 up to 10; wherein said contacting is carried out in the presence of hydrogen under hydrogenation conditions; wherein said hydrogenation conditions comprise a temperature in the range of 25° up to 400° C., and a pressure in the range of 100 up to 10,000 psig.

2. A process in accordance with claim 1 wherein said contacting is carried out in the further presence of in the range of 0.01 up to 2.0 wt % water, based on the total weight of reactants and solvent charged to the reactor.

3. A process in accordance with claim 1 wherein said catalyst is prepared by:
(a) contacting said support with zinc or a reducible compound thereof and palladium or a reducible compound thereof;
(b) and thereafter
contacting the zinc and palladium-treated support with a reducing atmosphere under conditions sufficient to cause reduction of at least a portion of the palladium to less than the +2 oxidation state.

4. A process in accordance with claim 1 wherein the hydrogen partial pressure falls within the range of 100 up to 10,000 psig.

5. A process in accordance with claim 1 wherein said hydrogenation conditions comprise a temperature in the range of 100° up to 350° C. and a pressure in the range of 100 up to 3500 psig.

6. A process in accordance with claim 1 wherein the liquid hourly space velocity falls within the range of about 0.01 up to 100 h$^{-1}$.

7. A process in accordance with claim 1 wherein the weight ratio of carbonyl-containing compound to catalyst falls within the range of 1:1 up to 10,000:1.

8. A process in accordance with claim 1 wherein the carbonyl-containing compound is selected from the group consisting of:

$$YO_2C-A-CO_2Y, \qquad (a)$$

wherein A is an alkylene moiety, an alkenylene moiety, or an alkynylene moiety having 1 up to 20 carbon atoms, or a substituted derivative thereof, or a cycloalkyl or cycloalkenyl moiety having 4–12 carbon atoms or a substituted derivative thereof; and wherein each Y is independently a $C_1$ up to $C_{12}$ alkyl, alkenyl or alkynyl radical or substituted derivative thereof;

$$B-CO_2Y \qquad (b)$$

wherein B is an alkyl, cycloalkyl, alkenyl, cycloalkenyl, alkynyl or cycloalkynyl radical, or substituted derivative thereof, having 1 up to 20 carbon atoms; and
wherein Y is defined as above;

wherein Q is an alkyl, cycloalkyl, alkenyl, cycloalkenyl, alkynyl or cycloalkynyl radical having 1 up to 20 carbon atoms or substituted derivatives thereof; and
mixtures of any two or more thereof.

9. A process in accordance with claim 8 wherein the carbonyl-containing compound comprises a dialkyl adipate.

10. A process in accordance with claim 9 wherein said alkyl radical has in the range of 1 up to 6 carbon atoms.

11. A process in accordance with claim 8 wherein the carbonyl-containing compound comprises a dialkyl cyclohexanedicarboxylate.

12. A process in accordance with claim 11 wherein said alkyl radical has in the range of 1 up to 6 carbon atoms.

13. A process in accordance with claim 8 wherein the carbonyl-containing compound is selected from the group consisting of an alkyl oleate, an alkyl stearate, an alkyl linoleate, an alkyl linolenate, an alkyl α-eleostearate, an alkyl β-eleostearate, and mixtures of any two or more thereof.

14. A process in accordance with claim 13 wherein said alkyl radical has in the range of 1 up to 6 carbon atoms.

15. A process in accordance with claim 8 wherein the carbonyl-containing compound comprises a dialkyl butanedicarboxylate.

16. A process in accordance with claim 15 wherein said alkyl radical has in the range of 1 up to 6 carbon atoms.

17. A process in accordance with claim 8 wherein the carbonyl-containing compound comprises a glycerol ester.

18. A process in accordance with claim 17 wherein said alkyl radical has in the range of 1 up to 6 carbon atoms.

19. A process in accordance with claim 8 wherein the carbonyl-containing compound comprises a dialkyl glutarate.

20. A process in accordance with claim 19 wherein said alkyl radical has in the range of 1 up to 6 carbon atoms.

21. A process in accordance with claim 8 wherein the carbonyl-containing compound is selected from the group consisting of dialkyl fumarates, succinates, maleates, and mixtures of any two or more thereof.

22. A process in accordance with claim 21 wherein said alkyl radical has in the range of 1 up to 6 carbon atoms.

23. A process in accordance with claim 8 wherein the carbonyl-containing compound comprises an alkyl decanoate.

24. A process in accordance with claim 8 wherein said alkyl radical has in the range of 1 up to 6 carbon atoms.

25. A process in accordance with claim 8 wherein the carbonyl-containing compound comprises an alkyl dodecanoate.

26. A process in accordance with claim 25 wherein said alkyl radical has in the range of 1 up to 6 carbon atoms.

27. A process in accordance with claim 8 wherein the carbonyl-containing compound is selected from the group consisting of alkyl acetates, propionates, butyrates, valerates, caproates, and mixtures of any two or more thereof.

28. A process in accordance with claim 27 wherein said alkyl radical has in the range of 1 up to 6 carbon atoms.

29. A process in accordance with claim 3 wherein the palladium and zinc treated support is calcined prior to said contacting with a reducing atmosphere; wherein said calcination is carried out in the presence of an oxygen-containing gas at a temperature in the range of 200° up to 400° C. for a time sufficient to activate said palladium and said zinc components.

30. A process in accordance with claim 1 wherein said catalyst is prepared by:
  (a) contacting said support with at least one of zinc or a reducible compound thereof and palladium or a reducible compound thereof; then
  (b) contacting said support again with at least one member selected from the group consisting of palladium or a reducible compound thereof and zinc or a reducible compound thereof, with the proviso that said support is ultimately contacted with both palladium and zinc; and thereafter
  (c) contacting the zinc and palladium-treated support with a reducing atmosphere under conditions sufficient to cause reduction of at least a portion of the palladium to less than the +2 oxidation state.

31. A process in accordance with claim 30 wherein the palladium or zinc treated support is calcined prior to said Step (b) contacting, wherein said calcination is carried out in the presence of an oxygen-containing gas at a temperature in the range of 200° up to 400° C. for a time sufficient to activate said palladium or zinc component.

32. A process in accordance with claim 30 wherein the palladium and zinc treated support is calcined prior to said contacting with a reducing atmosphere; wherein said calcination is carried out in the presence of an oxygen-containing gas at a temperature in the range of 200° up to 400° C. for a time sufficient to activate said palladium and zinc components.

33. A process in accordance with claim 31 wherein the palladium and zinc treated support is calcined prior to said contacting with a reducing atmosphere; wherein said calcination is carried out in the presence of an oxygen-containing gas at a temperature in the range of 200° up to 400° C. for a time sufficient to activate said palladium and zinc components.

* * * * *